United States Patent
Choi et al.

(10) Patent No.: US 11,120,893 B2
(45) Date of Patent: Sep. 14, 2021

(54) SYSTEMS AND METHODS FOR PATIENT-SPECIFIC IMAGING AND MODELING OF DRUG DELIVERY

(71) Applicant: HeartFlow, Inc., Redwood City, CA (US)

(72) Inventors: Gilwoo Choi, Palo Alto, CA (US); Leo Grady, Millbrae, CA (US); Charles A. Taylor, Menlo Park, CA (US); Stanley C. Hunley, Menlo Park, CA (US)

(73) Assignee: HeartFlow, Inc., Redwood City, CA (US)

( * ) Notice: Subject to any disclaimer, the term of this patent is extended or adjusted under 35 U.S.C. 154(b) by 200 days.

(21) Appl. No.: 15/267,671

(22) Filed: Sep. 16, 2016

(65) Prior Publication Data
US 2017/0076062 A1    Mar. 16, 2017

Related U.S. Application Data

(60) Provisional application No. 62/219,490, filed on Sep. 16, 2015.

(51) Int. Cl.
| | |
|---|---|
| *G16C 20/30* | (2019.01) |
| *A61B 5/00* | (2006.01) |
| *G16H 50/50* | (2018.01) |
| *G16H 20/10* | (2018.01) |

(52) U.S. Cl.
CPC ............ *G16C 20/30* (2019.02); *A61B 5/4848* (2013.01); *G16H 20/10* (2018.01); *G16H 50/50* (2018.01)

(58) Field of Classification Search
None
See application file for complete search history.

(56) References Cited

U.S. PATENT DOCUMENTS

| | | | |
|---|---|---|---|
| 8,315,812 B2 * | 11/2012 | Taylor | ............... A61B 5/02007 702/19 |
| 2005/0075274 A1 | 4/2005 | Willmann | |
| 2009/0210209 A1 | 8/2009 | Bartfeld | |
| 2012/0022843 A1 | 1/2012 | Ionasec | |
| 2016/0306945 A1 | 10/2016 | Jiang | |

FOREIGN PATENT DOCUMENTS

| | | |
|---|---|---|
| WO | WO 2012/021307 A2 | 2/2012 |
| WO | WO 2015/085276 | 6/2015 |

OTHER PUBLICATIONS

Liu et al. (Reviews in Nanoscience and Nanotechnology vol. 1, pp. 66-83, 2012).*
Jamei et al. (Expert Opinion on Drug Metabolism and Toxicology (2009) vol. 5:211-233).*
International Search Report issued in related international application No. PCT/US2016/052301, dated Jan. 2, 2017 (12 pages).

* cited by examiner

*Primary Examiner* — Lori A. Clow
(74) *Attorney, Agent, or Firm* — Bookoff McAndrews, PLLC

(57) ABSTRACT

Systems and methods are disclosed for providing personalized chemotherapy and drug delivery using computational fluid dynamics and medical imaging with machine learning from a vascular anatomical model. One method includes receiving a patient-specific anatomical model of at least one vessel of the patient and a target tissue where a drug is to be supplied; receiving patient-specific information defining the administration of a drug; deriving patient-specific data from the patient specific anatomical model and/or the patient; determining one or more blood flow characteristics in a vascular network leading to the one or more locations in the target tissue where drug delivery data will be estimated or measured, using the patient-specific anatomical model and the patient-specific data; and computing drug delivery data at the one or more locations in the target tissue using transportation, spatial, and/or temporal distribution of the drug particles.

20 Claims, 6 Drawing Sheets

SYSTEMS AND METHODS FOR PATIENT-SPECIFIC IMAGING AND MODELING OF DRUG DELIVERY

RELATED APPLICATION(S)

This application claims priority to U.S. Provisional Application No. 62/219,490 filed Sep. 16, 2015, the entire disclosure of which is hereby incorporated herein by reference in its entirety.

FIELD OF THE DISCLOSURE

Various embodiments of the present disclosure relate generally to drug delivery assessment, treatment planning, and related methods. More specifically, particular embodiments of the present disclosure relate to systems and methods for patient-specific imaging and modeling of drug delivery, e.g., for chemotherapy.

BACKGROUND

Cancer affects millions of people worldwide and is one of the most common causes of death. Chemotherapy is one form of cancer treatment in which patients are given one or more drugs as part of a standardized regimen. The efficacy of chemotherapy may be influenced by the effectiveness of drug delivery to target organs in patients. The effectiveness of drug delivery may be shaped by factors including, but not limited to, the drug amount, drug concentration, administration location, frequency of dosage, type of therapy, and/or patient characteristics. For example, determining the optimal dose of drug agent may be important since over-dosing can cause serious side effects due to drug toxicity, and under-dosing can lead to reduced effectiveness of therapy.

Current methods of drug delivery, such as those using body surface area (BSA), are inaccurate because they do not account for inter-patient variations. For example, there is a fourfold to tenfold variation in cytotoxic drug clearance between individuals due to differing activity of drug elimination processes related to genetic and environmental factors. Thus, there is a desire for a drug delivery system and method that is personalized, in order to account for inter-patient variation, and accurate, in order to minimize toxicities and help to improve treatment outcomes of chemotherapy.

Furthermore, having an effective personalized and accurate drug delivery system and method may also improve treatments of other ailments. Coronary artery disease is a common ailment that may cause blood vessels supplying blood to the heart to develop lesions, such as a stenosis (abnormal narrowing of a blood vessel). The presence or absence of stenosis, thrombosis and other circulatory conditions can affect blood flow characteristics along with drug delivery patterns. One of the treatments for coronary artery disease, percutaneous coronary intervention, involves treating the stenotic (narrowed) coronary arteries of the heart. While percutaneous coronary intervention runs the risk of generating a reappearance of stenosis (restenosis), an effective delivery of drug agents for percutaneous coronary intervention can help reduce restenosis rates. Thus, there is a desire for a system and method to assess the effectiveness of drug delivery by evaluating convection, diffusion, and/or metabolism rates throughout the circulatory system based on the blood flow characteristics.

The foregoing general description and the following detailed description are exemplary and explanatory only and are not restrictive of the disclosure.

SUMMARY

According to certain aspects of the present disclosure, systems and methods are disclosed for providing personalized chemotherapy and drug delivery by using computational fluid dynamics and/or machine learning from a vascular anatomical model.

One method includes: receiving a patient-specific anatomical model of at least one vessel of the patient and a target tissue where a drug is to be supplied; receiving patient-specific information defining the administration of a drug; identifying one or more locations in the target tissue where drug delivery data will be estimated or measured; deriving patient-specific data from the patient specific anatomical model and/or the patient; determining one or more blood flow characteristics in a vascular network leading to the one or more locations in the target tissue where drug delivery data will be estimated or measured, using the patient-specific anatomical model and the patient-specific data; determining the transportation, spatial, and/or temporal distribution of the drug particles in one or more locations in the vascular network using the patient-specific information defining the administration of the drug; and computing drug delivery data at the one or more locations in the target tissue using the transportation, spatial, and/or temporal distribution of the drug particles.

In accordance with another embodiment, a system is disclosed for estimating drug delivery at a target tissue. The system comprises: a data storage device storing instructions for estimating drug delivery at a target tissue; and a processor configured for: receiving a patient-specific anatomical model of at least one vessel of the patient and a target tissue where a drug is to be supplied; receiving patient-specific information defining the administration of a drug; identifying one or more locations in the target tissue where drug delivery data will be estimated or measured; deriving patient-specific data from the patient specific anatomical model and/or the patient; determining one or more blood flow characteristics in a vascular network leading to the one or more locations in the target tissue where drug delivery data will be estimated or measured, using the patient-specific anatomical model and the patient-specific data; determining the transportation, spatial, and/or temporal distribution of the drug particles in one or more locations in the vascular network using the patient-specific information defining the administration of the drug; and computing drug delivery data at the one or more locations in the target tissue using the transportation, spatial, and/or temporal distribution of the drug particles.

In accordance with yet another embodiment, a non-transitory computer readable medium for use on a computer system containing computer-executable programming instructions for estimating drug delivery at a target tissue is provided. The method includes: receiving a patient-specific anatomical model of at least one vessel of the patient and a target tissue where a drug is to be supplied; receiving patient-specific information defining the administration of a drug; identifying one or more locations in the target tissue where drug delivery data will be estimated or measured; deriving patient-specific data from the patient specific anatomical model and/or the patient; determining one or more blood flow characteristics in a vascular network leading to the one or more locations in the target tissue where drug delivery data will be estimated or measured, using the patient-specific anatomical model and the patient-specific data; determining the transportation, spatial, and/or temporal distribution of the drug particles in one or more locations in the vascular network using the patient-specific information defining the administration of the drug; and computing drug delivery data at the one or more locations in the target tissue using the transportation, spatial, and/or temporal distribution of the drug particles.

Additional objects and advantages of the disclosed embodiments will be set forth in part in the description that follows, and in part will be apparent from the description, or may be learned by practice of the disclosed embodiments. The objects and advantages on the disclosed embodiments will be realized and attained by means of the elements and combinations particularly pointed out in the appended claims.

It is to be understood that both the foregoing general description and the following detailed description are exemplary and explanatory only and are not restrictive of the detailed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

The efficacy of chemotherapy may be influenced by the effectiveness of drug delivery to target organs in patients. For the purposes of the disclosure: "patient" may refer to any individual or person for whom the effectiveness of drug delivery is being assessed, or any individual or person associated with the drug delivery assessment of one or more individuals. Determining the optimal dose of drug agent may be important; however, inter-patient variation in drug handling and a lack of accurate methods may pose challenges for determining the optimal dose. A personalized approach by monitoring drug levels in blood plasma and adjusting dose can minimize toxicities and help to improve treatment outcomes of chemotherapy. Moreover, effective delivery of drug agents for percutaneous coronary intervention can help reduce restenosis rates.

Given the potentially wide scope of this problem and utility, assessing the effectiveness of drug delivery can help clinicians determine treatment strategies for patients by evaluating drug delivery patterns along with convection, diffusion, and/or metabolism rates throughout the circulatory system based on the flow characteristics. The present disclosure describes systems and methods for providing personalized chemotherapy and drug delivery modeling using computational fluid dynamics and medical imaging with machine learning from a vascular/anatomical model. While the following embodiments may be directed to brain tumor and coronary lesions, the same system and method could be applied to creating patient-specific models of chemotherapy and drug delivery in other oncological diseases, including breast cancer, prostate cancer, liver cancer, colon cancer, lung cancer, and/or cervical cancer. Furthermore, the framework could be extended to assess patient-specific models of implantable drug delivery devices, including nanoparticles and hydrogels. In some cases, a "particle" may refer to a small unit of drug (e.g., molecule) that may be released into the patient's blood stream or transported to the target tissue.

Figure 1:
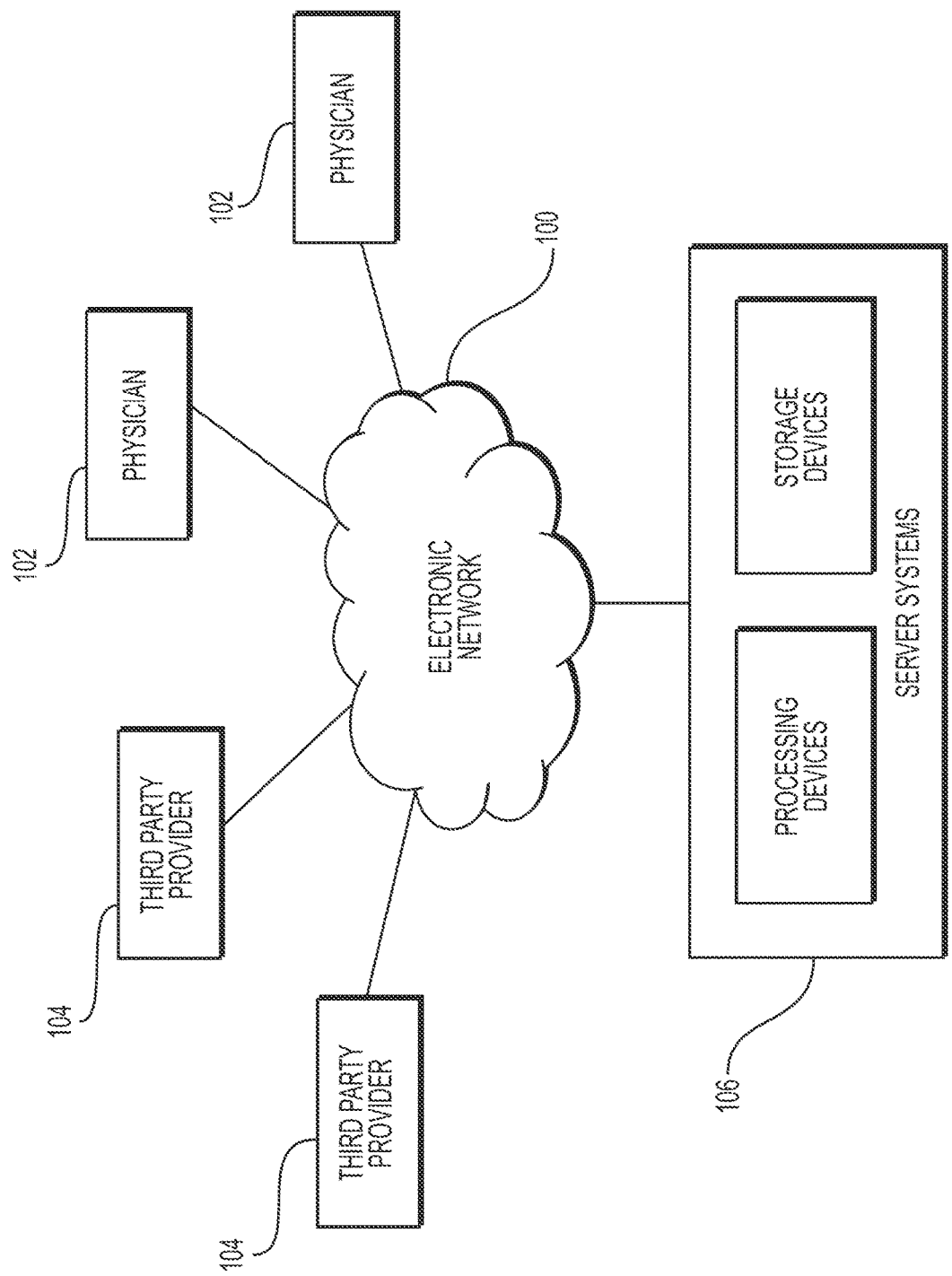
FIG. 1 is a block diagram of an exemplary system and network for providing personalized chemotherapy and drug delivery, according to an exemplary embodiment of the present disclosure.
Figure 2:
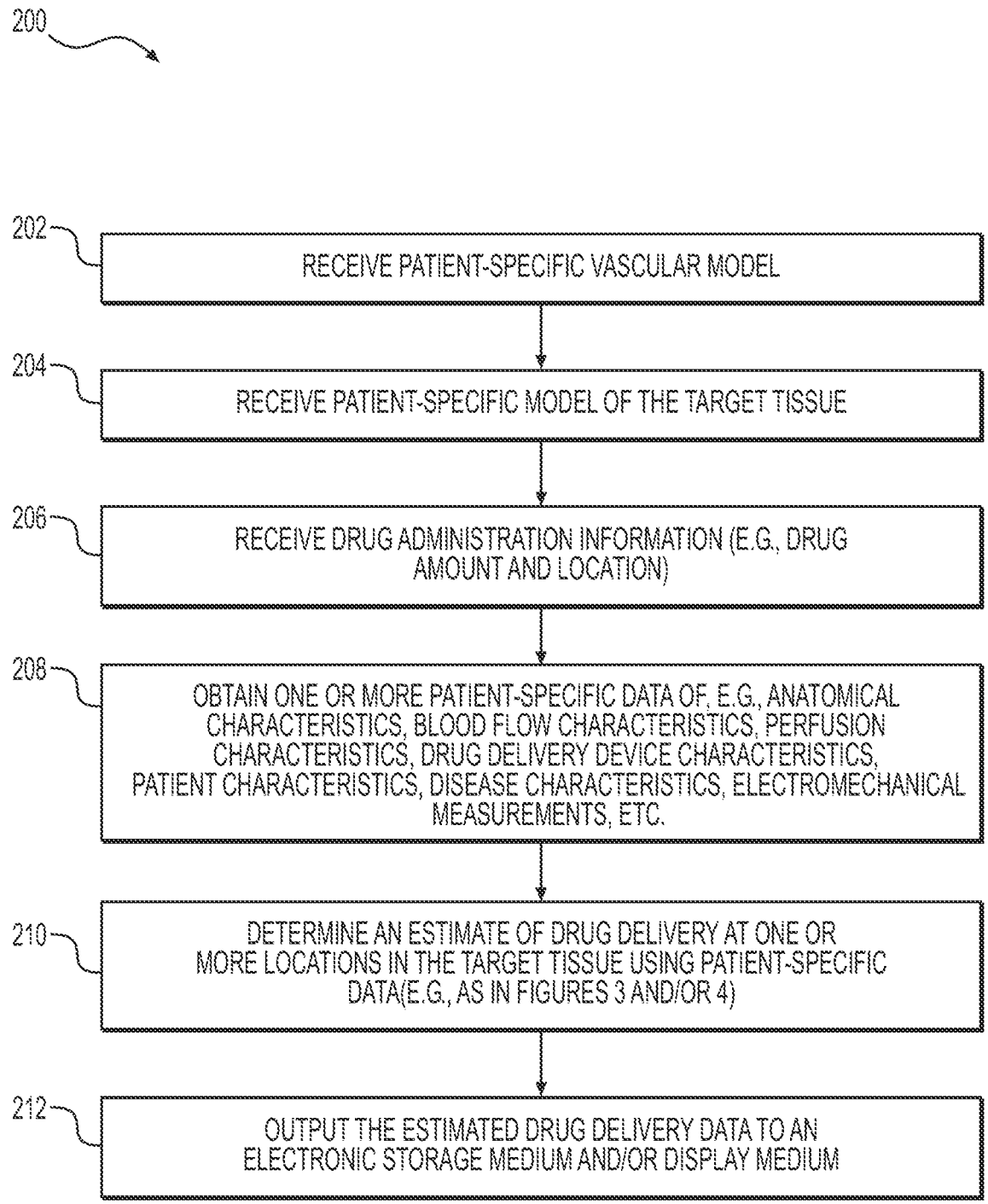
FIG. 2 is a block diagram of an exemplary method of estimating drug delivery at a target tissue.
Figure 3:
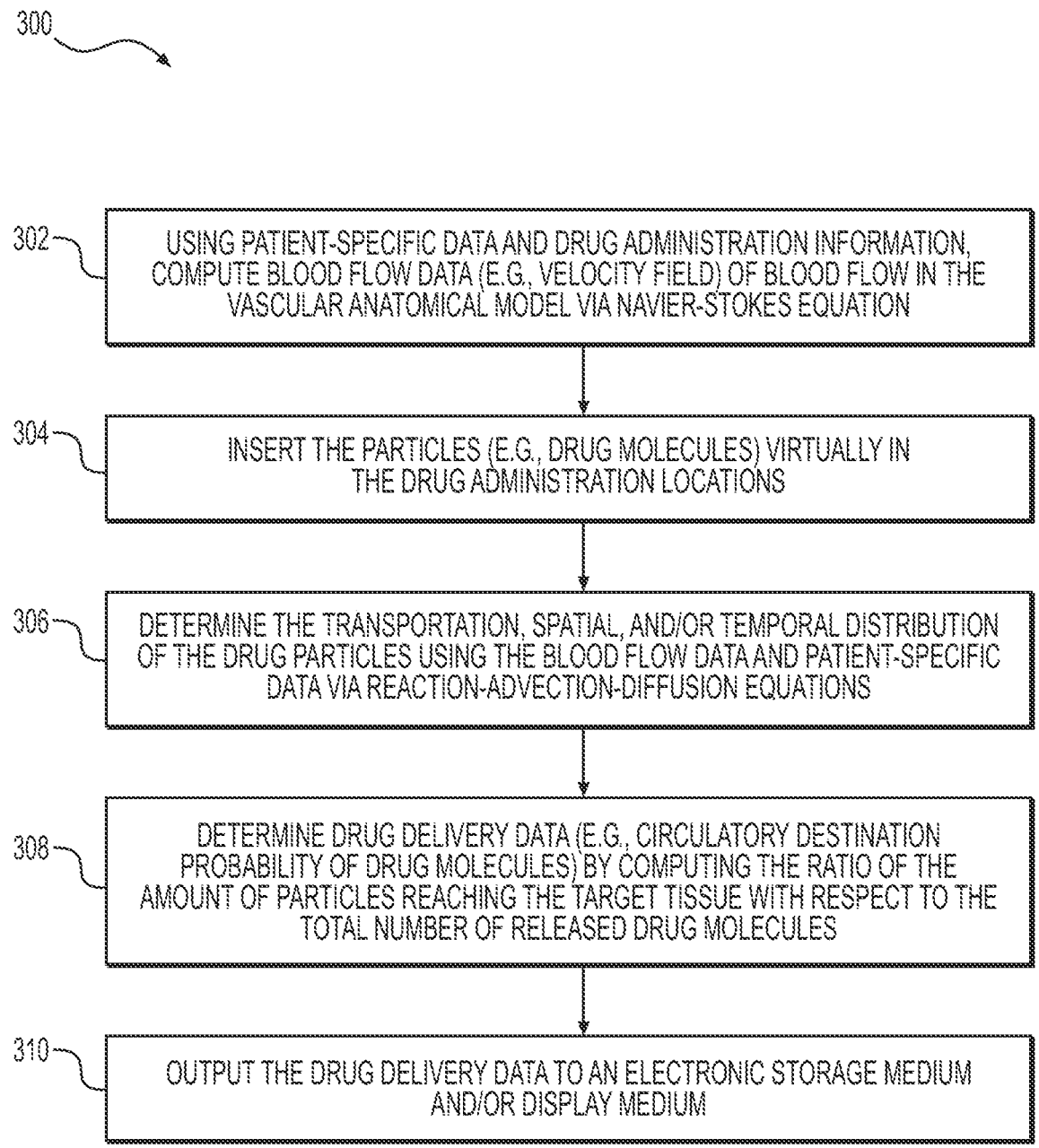
FIG. 3 is a block diagram of an exemplary method of determining drug delivery data at one or more locations in the target tissue using patient-specific data using computational fluid dynamics.
Figure 4:
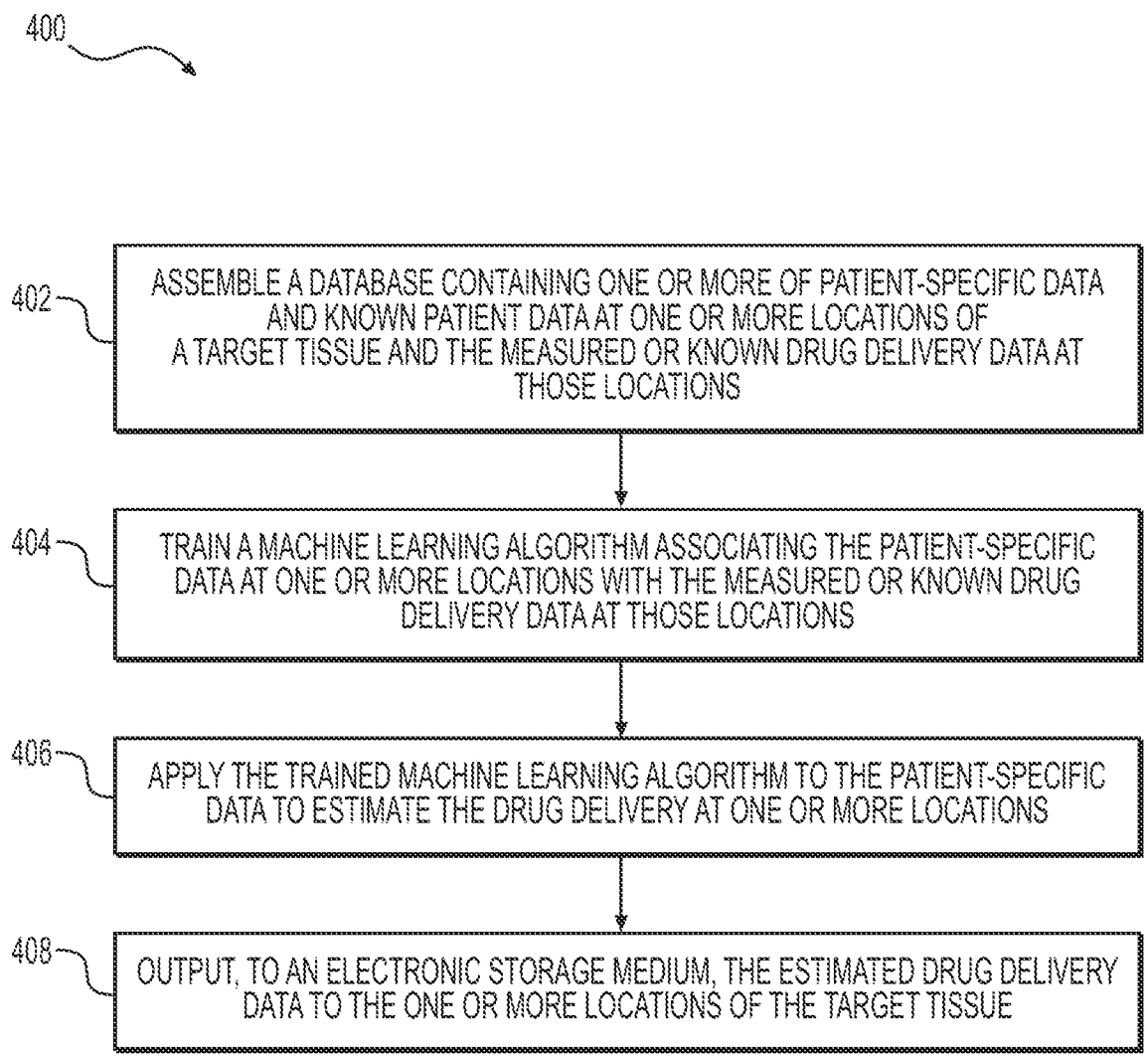
FIG. 4 is a block diagram of an exemplary method of determining drug delivery data at one or more locations in the target tissue by training a machine learning algorithm using patient-specific data.

The steps described in the methods may be performed in any order, or in conjunction with any other step. It is also contemplated that one or more of the steps may be omitted for performing the methods described in the present disclosure. In general, FIG. 1 provides depicts an overview of a system and network of the current disclosure; FIG. 2 illustrates a general embodiment of a method for estimating drug delivery in the target tissue; FIG. 3 and FIG. 4 illustrate step 210 within method 200 disclosed in FIG. 2, in more detail; and FIGS. 5 and 6 expand the general embodiment of FIG. 2 into a personalized chemotherapy and drug delivery system and method.

Referring now to the figures, FIG. 1 depicts a block diagram of an exemplary system 100 and network for providing personalized chemotherapy and drug delivery, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific data, such as medical image characteristics, anatomical characteristics, perfusion territories, blood supply to the target tissue, blood flow characteristics, patient characteristics, disease burden characteristics, and/or electromechanical measurements. Physicians 102 and/or third party providers 104 may transmit the patient-specific data to server systems 106 over the electronic network 101. Server systems 106 may include storage devices for storing images and data received from physicians 102 and/or third party providers 104. Server systems 106 may also include processing devices for processing images and data stored in the storage devices. For purposes of disclosure, "electronic storage devices" or "electronic storage media" may include, but are not limited to, a hard drive, network drive, cloud drive, mobile phone, tablet, or the like that may or may not be affixed to a display screen.

FIG. 2 depicts a general embodiment of an exemplary method 200 for estimating drug delivery at a target tissue. One or more steps of method 200 may be performed by a processor of server systems 106. In one embodiment, step 202 may include receiving a patient specific vascular anatomical model in an electronic storage medium of the server system 106. Specifically, receiving the patient-specific anatomical model may include either generating the patient-specific anatomical model at the server system 106, or receiving one over an electronic network (e.g., electronic network 100). The patient specific vascular anatomical model may include, but is not limited to, the patient's cerebrovascular system, cardiovascular system, and/or the vasculature perfusing the breasts, prostate, liver, colon, lung, and/or cervix. In one embodiment, the vascular anatomical model may be derived from images of the person acquired using one or more available imaging or scanning modalities (e.g., computed tomography (CT) scans, magnetic resonance (MR) imaging, micro-computed tomography (μCT) scans, micro-magnetic resonance (μMR) imaging, dual energy computed tomography scans, ultrasound imaging, single photon emission computed tomography (SPECT) scans, or positron emission tomography (PET) scans). The vascular anatomical model may be obtained through segmentation of an imaging study, including, but not limited to, images obtained from one or more said available imaging or scanning modalities.

Step 204 may include receiving a patient specific model of the target tissue in an electronic storage medium. For purposes of disclosure, a "target tissue" may refer to the tissue and/or organ in which the blood supply and/or drug delivery data may be estimated. In one embodiment, the target tissue may be found in an organ afflicted with cancerous growth, including, but not limited to the brain, one or more breasts, the prostate, liver, colon, lung, and/or cervix. In one embodiment, the target tissue may be found in vasculature affected with thrombosis, including but not limited to the coronary, aortic, or cerebrovascular systems, peripheral vasculature perfusing one or more muscles, renal vasculature supplying the kidney, and/or visceral vasculature supplying the bowels, liver, and/or spleen. In one embodiment, the patient specific model of the target tissue may be obtained through segmentation of an imaging study, including, but not limited to, images obtained from one or more said available imaging or scanning modalities.

Step 206 may include receiving patient-specific drug administration information. In one embodiment, drug administration information may include one or more drug administration locations and the respective drug amounts inserted at the one or more drug administration locations. In another embodiment, drug administration information may include the administered drug concentration, administration frequency, administration time, type of therapy, and/or one or more routes of drug administration, with said routes including, but not limited to, oral administration, intravenous administration, or direct administration into the tumor and/or lesion.

Step 208 may include receiving or calculating one or more elements of patient-specific data. In one embodiment, the one or more patient-specific data elements may be extracted from the patient specific vascular anatomical model and/or patient specific model of a target tissue. In one embodiment, the patient-specific data may include, but are not limited to an estimate of one or more anatomical characteristics of the vessel model and/or target tissue model, for example, size (volume, surface area, mass, etc.), shape, tortuosity, length, thickness, number and length of branches, network topology, etc. In one embodiment, the patient-specific data may include, but are not limited to an estimate of the supplied blood to each area of the target tissue under one or more physiological states, and/or one or more blood flow characteristics, for example, fractional flow reserve (FFR), flow magnitude and direction, etc. The blood flow characteristics may be determined through several means, for instance, invasive measurement (e.g., through invasive FFR, thrombolysis in myocardial infarction (TIMI), microspheres, etc.), calculation using a blood flow simulation (e.g., a 3D or 1D fluid simulation model, calculation, transluminal attenuation flow encoding (TAFE), etc.), calculation using imaging characteristics (e.g., transluminal arterial gradient (TAG), corrected coronary opacification (CCO), etc.) and/or calculation using a machine learning estimation of blood supply based on anatomical or imaging features.

The patient-specific data may include, but are not limited to an estimate of the perfusion or diffusion territories of the target tissue related to the vascular model. This estimate may be determined, for instance, using a nearest-neighbor (Voronoi) approach to assigning locations in the target tissue to the closest supplying vessel in the vascular model, a microvascular estimation technique calculation from an anatomical model, including constrained constructive optimization.

Furthermore, the patient-specific data may include, but are not limited to an estimate of the perfusion or diffusion territories of the drug delivery device related to the release of particles into the blood flow. The estimate of the perfusion or diffusion territories may be determined by an exemplary method of using a thermodynamic model and mass transport models, including energy conservation or Fick's Laws of Diffusion, to simulate drug release assuming ionic equilibrium. In one embodiment, the estimate of the perfusion or diffusion territories may be determined by an exemplary method of using Multiphase Mixture Theory to simulate drug release driven by mechanical, chemical, or electrochemical potentials in response to shear, compression, or expansion flow.

Furthermore, the patient-specific data may include drug delivery device characteristics, including but not limited to, device size, particle properties (e.g., size, concentration, molecular weight, etc.), hydrogel polymer material properties (e.g., elastic modulus, cross-link density, solubility, porosity, matrix swelling, etc.), and/or operating parameters (e.g., temperature, solvent quality, pH, charge density, etc.), etc.

Furthermore, the patient-specific data may include, but are not limited to, medical images (e.g., a CT, MR, μCT, μMR, dual energy CT, ultrasound, PET, SPECT, etc.) in one or more physiological states (e.g., rest, stress, etc.) of the target tissue and/or vessels represented by the vascular model. Image characteristics of the target tissue or vessels may be received or calculated in one or more locations, including, but not limited to, local average intensities at one or more resolutions, differences of average intensities (e.g., calculated using wavelet bases such as Haar), texture characteristics (e.g., Haralick texture features), any standard image features, including histograms of gradients, SIFT, steerable filters, etc.

Furthermore, the patient-specific data may include, but are not limited to, patient characteristics, such as age, gender, smoking history, height, weight, body surface area (BSA), diabetic status, hypertensive status, ethnicity, family history, and/or genetic information.

Furthermore, the patient-specific data may include, but are not limited to, vascular or target tissue disease characteristics, including tumor size, degree of malignancy, location of tumor in the brain, tumor blood flow, oxygen transport, vascular endothelial growth factor distribution, extracellular pH, interstitial fluid pressure, interstitial fluid velocity, vascular permeability, tissue transport properties, angiogenic parameters (e.g., tumor blood volume), plaque burden, presence of adverse plaque characteristics (e.g., spotty calcification, low attenuation plaque, napkin ring sign, positive remodeling, thrombus formation, etc.), calcium score (patient-level or vessel-level), perfusion information, ejection fraction, wall motion, wall thickness, wall morphology, wall histology, etc.

Furthermore, the patient-specific data may include, but are not limited to electromechanical measurements, including ECG measurements or invasive EP measurements.

Step 210 may include determining one or more drug delivery data at one or more locations in the target tissue using one or more of the patient-specific data. In one embodiment, the drug delivery data may include an estimate of drug delivery at one or more locations in the target tissue. The determination of drug delivery data may be performed by computational simulations of tumor vasculature hemodynamics (e.g., FIG. 3) and/or training a machine learning algorithm using a database of patients with known drug delivery (e.g. FIG. 4).

Step 212 may include outputting the estimated drug delivery data to an electronic storage medium and/or a display medium. In one embodiment, the drug delivery estimates may be displayed in greyscale or color, in 2D or 3D, overlaid on the anatomical model of the target tissue, and/or overlaid on an image of the target tissue.

FIG. 3 depicts an exemplary embodiment of method 300 for performing step 210 of FIG. 2, which may include determining drug delivery data at one or more locations in the target tissue by performing computational simulations of tumor vasculature hemodynamics on patient-specific data. In one embodiment, method 300 may include using Navier-Stokes equation, computational fluid dynamics (or approximations thereof), and or reaction-advection-diffusion equations to determine blood flow characteristics, and then using drug administration information and blood flow characteristics to estimate the transportation, spatial, and/or temporal distribution of the drug. For purposes of disclosure, "drug administration information" may refer to details regarding the administration of a drug or therapy to a patient, including, but not limited to, administered drug amount, administered drug concentration, administration location, administration frequency, route of drug administration, administration time, type of therapy, etc. One or more steps of method 300 may be performed by a processor of server systems 106.

In one embodiment, the drug delivery data in the one or more locations in the target tissue may be estimated or calculated from the transportation, spatial, and/or temporal distribution of the drug. In another embodiment, the transportation, spatial, and/or temporal distribution of the drug may be used to train a machine learning algorithm for estimating or calculating the drug delivery data in the one or more locations in the target tissue. The method of FIG. 3 may be performed by server systems 106, based on patient-specific data received from physicians 102 and/or third party providers 104 over the electronic network 100. For purposes of disclosure, "drug delivery data" may refer to an estimate of the amount of drug delivered to the one or more locations in the target tissue, an estimate of the concentration of drug particles delivered to the one or more locations in the target tissue; the circulatory destination probability of the drug particles released at the drug delivery location to the target tissue, which may be defined as the ratio of the amount of drug particles reaching the target tissue with respect to the total number of released drug particles, the transportation, spatial, and/or temporal distribution of the drug, an estimate of the blood flow data; or a combination thereof.

Step 302 may include computing the blood flow characteristics in the patient specific vascular anatomy. In one embodiment, computing the blood flow data may include solving the Navier-Stokes equation, or a modified Navier-Stokes equation with Darcy's law term for a flow through a porous medium, numerically under the patient's physiologic conditions (e.g., hyperemic or rest state, interstitial fluid pressure, tumor growth state, etc.). In one embodiment, the blood flow data may include the velocity field of blood flow in the heart, the coronary, cerebral, carotid vasculature, the aortic arch, or any other vascular network. In one embodiment, the blood flow data may include the velocity field of venous circulation and/or micro-circulation, as well as arterial circulation.

Step 304 may include inserting the drug amounts in the received one or more drug administration locations. In one embodiment, the drug amounts may be administered virtually so as to simulate drug delivery.

Step 306 may include determining the transportation, spatial, and/or temporal distribution of the drug particles. In one embodiment, determining drug particle distribution may utilize an ordinary differential equation of a form characteristic of $x \cdot (t) = u(x,t)$; $x(t_0) = x_0$, using an appropriate numerical method, where $u(x,t)$ may be the velocity field and $x(t)$ may be the location of the particle at time t. The size and amount of particles may be determined as a prescribed dosage of administered drug. In another embodiment, determining drug particle distribution may utilize an equation describing drug transport, which may be described as $$\frac{\partial C_F}{\partial t} + v_F \cdot \nabla C_F = \nabla \cdot D \nabla C_F,$$

where $C_F$ may be the drug concentration in the fluid, t may be time, $V_F$ may be fluid velocity, and D may be the diffusion tensor with the effective diffusivity factors of the drug in the fluid. In one embodiment, varying mechanical and transport properties can be assigned to each of the three layers (e.g., intima, media, adventitia) in the vessel wall. Non-Newtonian rheological properties may also be considered for tumor microvasculature hemodynamics.

Step 308 may include determining the drug delivery data in the one or more locations in the target tissue. In one embodiment, the drug delivery data may be determined from the transportation, spatial, and/or temporal distribution of drug particles, as determined in step 306. In one embodiment, the drug delivery data may be determined from training a machine learning algorithm that utilizes the transportation, spatial, and/or temporal distribution of drug particles (e.g., method 400). In one embodiment, the drug delivery data may include the circulatory destination probability of drug molecules in the one or more locations. The circulatory destination probability may be computed from the ratio of the amount of particles reaching a location in the target tissue with respect to the total number of released particles. In one embodiment, step 308 may be performed by a processor.

Step 310 may include outputting the estimated drug delivery data to an electronic storage medium and/or display medium. In one embodiment, the drug delivery data may include the transportation, spatial, and/or temporal distribution of the drug. In one embodiment, the drug delivery estimates may be displayed in greyscale or color, in 2D or 3D, overlaid on the anatomical model of the target tissue, and/or overlaid on an image of the target tissue.

FIG. 4 depicts an exemplary embodiment of method 400 for performing step 210 of FIG. 2, which may include determining drug delivery data at one or more locations in the target tissue by training a machine learning algorithm on patient-specific data. Alternately, method 400 may be performed subsequent to method 300 as a means to complete step 210 of FIG. 2, which may include using computational simulations of tumor vasculature hemodynamics and training a machine learning algorithm on patient-specific data in order to determine drug delivery data.

In one embodiment, method 400 may include determining drug delivery data at one or more locations in the target tissue by training a machine learning algorithm on patient-specific data. The method of FIG. 4 may be performed by server systems 106, based on patient-specific data received from physicians 102 and/or third party providers 104 over the electronic network 100. One or more steps of method 400 may be performed by a processor.

In one embodiment, step 402 may include assembling a database containing one or more of the patient-specific data at one or more locations with the measured drug delivery data at those locations. For example, step 402 may include assembling a database of patients with known patient-specific data and known drug delivery data. The one or more patient-specific data may include a numerical description of physiological or phenotypic parameters of the patient and/or a description of the local geometry and biophysical characteristics at one or more locations. In one embodiment, the one or more patient-specific data may include blood flow data, transportation, spatial, and/or temporal distribution of drug particles, and/or circulatory destination probability of drug particles obtained from method 300. The measured or known drug delivery data at one or more locations may include, for example, one or more combinations of MR image, fluorodeoxyglucose positron emission tomography (FDG-PET) image, stress echo/MRI contractile reserve, multidetector CT, dual energy CT, μCT, μMR, etc.

Step 404 may include training a machine algorithm to map the patient-specific data for one or more locations to the drug delivery data at those locations. In one embodiment, the patient-specific data and drug delivery data may be obtained from a database of patients with known patient-specific data and known drug delivery data. The one or more patient-specific data may include a numerical description of physiological or phenotypic parameters of the patient and/or a description of the local geometry and biophysical characteristics at one or more locations. Furthermore, one or more patient-specific data may include blood flow data, transportation, spatial, and/or temporal distribution of drug particles, and/or circulatory destination probability of drug particles obtained from method 300. The machine learning algorithm may take many forms, for example, one or more algorithms implementing a multilayer perceptron, deep learning, support vector machines, random forests, k-nearest neighbors, Bayes networks, etc.

Step 406 may include applying the trained machine learning algorithm to the new patient-specific data to estimate the drug delivery data at one or more locations in the target tissue. In one embodiment, the machine learning algorithm would be trained with a database of patients with known patient-specific data and known drug delivery data, and will be applied to the patient-specific data of a new patient to estimate the drug delivery data at one or more locations of the new patient's body.

In one embodiment, step 408 may include outputting, to an electronic storage medium and/or display screen, the estimated drug delivery data at one or more locations in the target tissue. The drug delivery data may include the amount of drug delivered to one or more locations on the target tissue. The output drug delivery data may be displayed in greyscale or color in 2D or 3D, overlaid on the anatomical model of the target tissue, and/or overlaid on an image of the target tissue. In the output model, one or more locations in the target tissue may be associated with a circulatory destination probability of drug particles, which may be defined as the ratio of the amount of drug particles reaching the target tissue with respect to the total number of released drug particles. In one embodiment, one or more locations in the target tissue may be associated with the transportation, spatial, and/or temporal distribution of the drug delivered.

Figure 5:
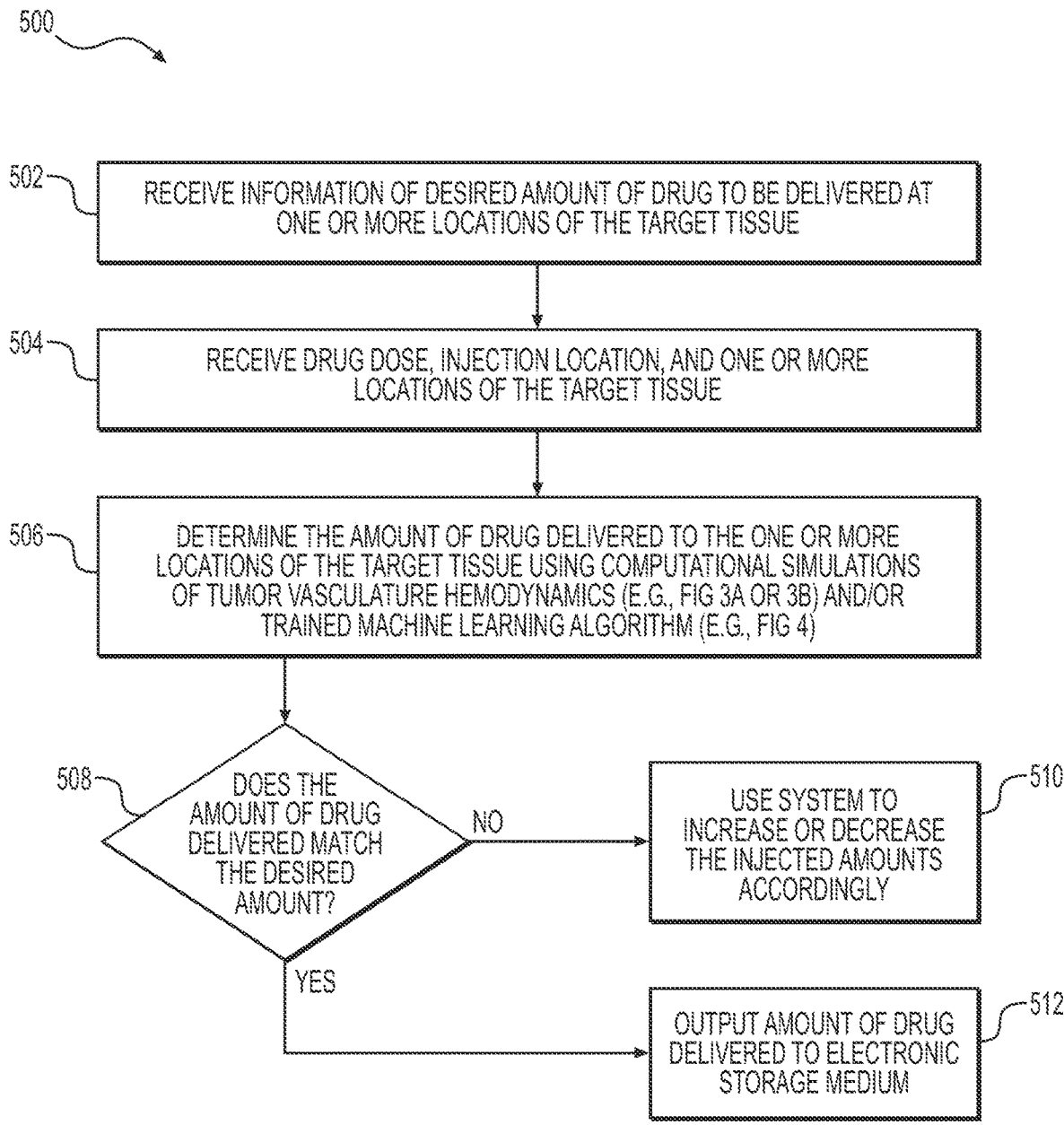
FIG. 5 is a block diagram of an exemplary method of using the system and method described in method 200 to regulate drug administration until the actual drug delivery data matches, or falls within the range of, a desired drug delivery data.

FIG. 5 depicts an exemplary embodiment of method 500 for using the system and method described in method 200 to regulate drug administration until the amount of drug delivered matches, or falls within the range of, a desired drug delivery amount. One or more steps of method 500 may be performed using a processor of server systems 106.

In one embodiment, step 502 may include receiving information on the desired drug delivery data for one or more locations in the target tissue. For example, step 502 may include receiving information on the desired amount of drug to be delivered to one or more locations on a tumor or lesion.

Step 504 may include receiving patient-specific drug administration information. For example, drug administration information may include one or more drug administration locations and the respective drug amounts inserted at the one or more drug administration locations. In another example, drug administration information may also include one or more of the administered drug concentration, administration frequency, administration time, type of therapy, and/or one or more routes of drug administration, with said routes including, but not limited to, oral administration, intravenous administration, or direct administration into the tumor and/or lesion.

Step 506 may include determining the drug delivery data at one or more locations on the target tissue by using computed simulations of tumor vasculature hemodynamics (e.g., FIG. 3) and/or by applying a trained machine learning algorithm (e.g., FIG. 4). For example, step 506 may include determining the amount of drug delivered to the one or more locations on the target tissue. In one embodiment, step 506 may be performed by a processor.

In one embodiment, subsequent to step 506, step 508 may include determining whether the drug delivery data at one or more locations on the target tissue matches, or falls within the range of, the desired drug delivery data at those locations. For example, step 508 may include determining whether the amount of drug delivered to a location on the target tissue matches the desired amount of drug to be delivered to that location. Step 508 may be performed by a processor.

If, subsequent to step 508, the actual drug delivery data does not match or does not fall within the range of the desired drug delivery data for one or more locations on a target tissue, then, in one embodiment, step 510 may include adjusting the drug administration accordingly, and repeating step 504. For example, if the amount of drug delivered is greater than the desired amount of drug to be delivered, then the administered amount may be decreased or maintained. In another example, if the amount of drug delivered is less than the desired amount of drug to be delivered, then the administered amount may be increased or maintained. In one embodiment, if the amount of drug delivered does not match or does not fall within the range of the desired amount of drug to be delivered, then factors other than the administration amount may be adjusted. These said factors may include, but are not limited to, the one or more locations of the drug administration, the drug concentration, the route of drug administration, the type of therapy, and/or the frequency of drug insertion, etc.

If, subsequent to step 508, the amount of drug delivered matches or falls within the range of the desired amount of drug to be delivered, then, in one embodiment, step 512 may include outputting drug delivery data to an electronic storage medium and/or display medium. In one embodiment, the drug delivery data may include the amount of drug delivered to one or more locations on the target tissue. The output drug delivery data may be displayed in greyscale or color in 2D or 3D, overlaid on the anatomical model of the target tissue, and/or overlaid on an image of the target tissue.

Figure 6:
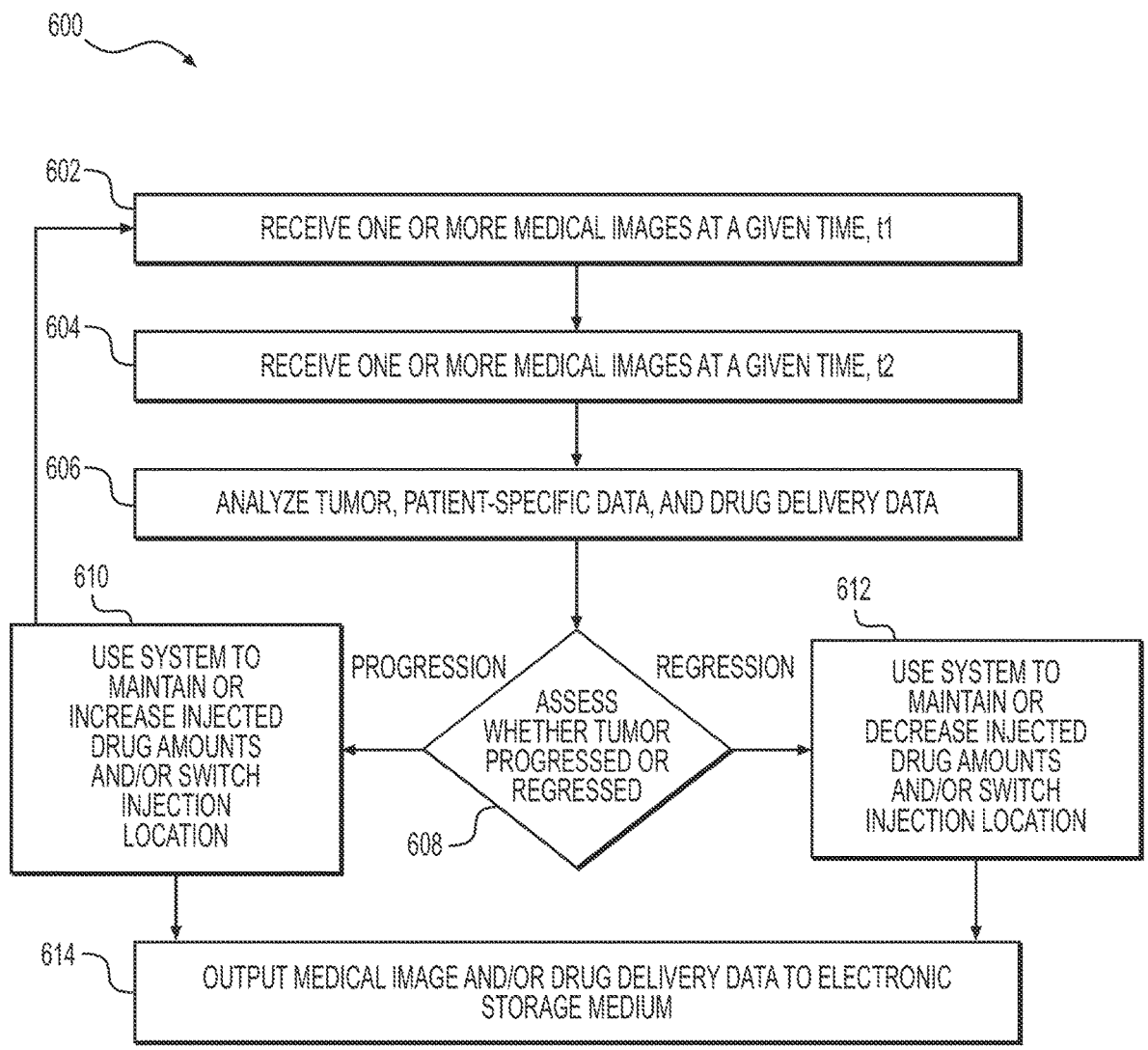
FIG. 6 is a block diagram of an exemplary method of using the system and method described in method 200 for simulating changes in drug delivery towards a target tissue by assessing the effectiveness of the drug delivery.

FIG. 6 depicts an exemplary embodiment of method 600 for using the system and method described in method 200 for simulating changes in tumor blood flow by assessing effectiveness of the drug delivery or therapy. One or more steps of method 600 may be performed using a processor of server systems 106.

Step 602 may include receiving one or more medical images at a given time, t1. The one or more medical images may be from one or more available scanning modalities. In one embodiment, the one or more medical images may be obtained using segmentation of an imaging study, including, but not limited to, images obtained from one or more said available imaging or scanning modalities.

Step 604 may include receiving one or more medical images at a given time, t2. The one or more medical images may be from one or more available scanning modalities. In one embodiment, the one or more medical images may be obtained using segmentation of an imaging study, including, but not limited to, images obtained from one or more said available imaging or scanning modalities. The segmentation of the images may be performed by a processor.

Step 606 may include comparing the tumor, lesion, patient-specific data, and/or drug delivery data extracted from the one or more medical images from different times. For example, the comparison may include determining whether intensity gradients between medical images from different times have a difference that is within a predetermined threshold.

Step 608 may include assessing the effectiveness of the current drug delivery system, subsequent to the comparison in step 606. In one embodiment, an assessment on the effectiveness of the current drug delivery system may include determining the status change of the tumor or lesion. For example, the status change of the tumor or lesion may be classified into one or more levels of progression and regression, and the effectiveness of the drug delivery system may be correlated with the level of regression in the tumor or lesion. The status change may be determined by comparing the images received at step 602 and step 604. Determining the status change of the tumor or lesion may also be aided by patient-specific data and/or drug delivery data.

If, subsequent to step 608, the current drug delivery system is deemed to be insufficiently effective, and/or the status of the tumor or lesion has progressed, then, in one embodiment, step 610 may include using the system described in method 200 to increase or maintain the drug administration amount, and then repeating step 602. In one embodiment, step 610 may include adjusting factors other than the drug administration amount. These said factors may include, but are not limited to, the one or more locations of the drug administration, the drug concentration, the route of drug administration, the type of therapy, and/or the frequency of drug insertion, etc.

If, subsequent to step 608, the current drug delivery system is deemed to be effective, and/or the status of the tumor or lesion has regressed, then, in one embodiment, step 612 may include using the system described in method 200 to maintain or decrease the drug administration amount, and then repeating step 602. In one embodiment, step 612 may include adjusting factors other than the drug administration amount. These said factors may include, but are not limited to, the one or more locations of the drug administration, the drug concentration, the route of drug administration, the type of therapy, and/or the frequency of drug insertion, etc.

In one embodiment, subsequent to step 608, step 614 may include outputting the one or more medical images, tumor or lesion status, and/or drug delivery data to an electronic storage medium and/or display. In one embodiment, the one or more medical images, tumor or lesion status, and/or drug delivery data may be displayed in greyscale or color, in 2D or 3D, overlaid on the anatomical model of the target tissue, and/or overlaid on an image of the target tissue.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of estimating drug delivery at a target tissue, the method comprising:
  receiving a patient-specific anatomical model of at least one vessel of the patient and a target tissue where a drug is to be supplied;
  receiving patient-specific information defining administration of a drug to the patient;
  identifying one or more locations in the target tissue where drug delivery data will be computed;
  deriving patient-specific data from the patient-specific anatomical model and/or the patient, the patient-specific data including one or more physiological conditions;
  determining, by measuring or calculating, one or more personalized blood flow characteristics in a vascular network leading to the one or more locations in the target tissue where drug delivery data will be computed, using the patient-specific anatomical model, patient-specific information defining the administration of the drug and the patient-specific data including the one or more physiological conditions;
  simulating drug delivery by virtually modeling the administration of drug particles into the vascular network of the patient-specific anatomical model upstream from the one or more locations in the target tissue;

calculating a transportation, spatial, and/or temporal distribution of the drug particles in one or more locations of the vascular network using size and amount of the drug particles, one or more equations describing drug transport, the patient-specific information defining the administration of the drug including size and amount of the drug particles, and calculated one or more personalized blood flow characteristics, wherein the amount of the drug particles are calculated based on a prescribed dosage of the drug;

determining a ratio of the drug particles reaching the target tissue to the drug particles administered in total based on the calculating the distribution of the drug particles to the one or more locations of the vascular network and the calculated one or more personalized blood flow characteristics;

computing personalized drug delivery data at the one or more locations in the target tissue of the patient-specific anatomical model using the patient-specific data derived from the patient-specific anatomical model and the transportation, spatial, and/or temporal distribution of the drug particles, the personalized drug delivery data including a circulatory destination probability of the drug particles administered into the vascular network leading to the target tissue based on the ratio of the drug particles reaching the target tissue to the drug particles administered in total;

outputting the personalized drug delivery data in three-dimensional display overlaid on the patient-specific anatomical model to an electronic storage medium and/or display medium; and modifying drug administration to cause the computed personalized drug delivery data including the ratio of the drug particles reaching the target tissue to the drug particles administered in total in the target tissue to be within a range of desired drug delivery data in the target tissue.

2. The method of claim 1, wherein the patient-specific information defining the administration of a drug includes one or more of a drug administration amount, a drug concentration, an administration location, an administration frequency, a route of drug administration, an administration time, a type of therapy, or a combination thereof.

3. The method of claim 1, wherein the patient-specific data includes: a vascular anatomical image characteristic; a target tissue image characteristic; an estimated perfusion territory in the target tissue; an estimated blood supply to the target tissue; an estimated blood flow data; a patient characteristic; a disease burden characteristic; an electromechanical measurement; or a combination thereof.

4. The method of claim 1, wherein the personalized drug delivery data includes, one or more of:
an estimate of the amount of drug delivered to the one or more locations in the target tissue;
an estimate of a concentration of drug particles delivered to the one or more locations in the target tissue;
an estimate of blood flow data; or a combination thereof.

5. The method of claim 1, wherein the personalized blood flow characteristics include, one or more of,
a velocity field of blood flow in the patient's vasculature, an estimated blood supply in the patient's vasculature, or any patient-specific hemodynamic characteristic that affects the distribution of drug particles along the vascular network.

6. The method of claim 1, wherein the patient-specific anatomical model includes, one or more of,
vessels that supply blood to a diseased or cancerous tissue or organ, or
vessels that supply blood to an area affected by a stenosis, or
vessels that supply blood to an area affected by a thrombosis.

7. The method of claim 1, wherein the target tissue is, one or more of:
a tissue or organ affected with tumorous growth, including, one or more of, a brain, breast, prostate, cervix, lung, skin, colon, or stomach;
a tissue or organ affected by a stenosis within a vascular and/or microvascular network; or
a tissue or organ affected by a thrombosis within the vascular and/or microvascular network.

8. The method of claim 1, further including:
receiving the desired drug delivery data in the target tissue; and
assessing effectiveness of a current drug delivery system by comparing the computed personalized drug delivery data including the ratio of the drug particles reaching the target tissue to the drug particles administered in total in the target tissue with the desired drug delivery data in the target tissue.

9. The method of claim 1, wherein modifying the drug administration includes systematically adjusting one or more of a drug amount, a drug concentration, a drug administration location, a drug administration frequency, a route of drug administration, an administration time, a type of therapy, or a combination thereof, in order to increase effectiveness of a current drug delivery system.

10. The method of claim 1, further including:
receiving, at different time points, one or more medical images of patients;
extracting patient-specific data from the one or more medical images;
assessing an effectiveness of the current drug delivery system by comparing the patient-specific data extracted from the one or more medical images; and
reconfiguring the drug administration in order to increase effectiveness of a current drug delivery system.

11. The method of claim 10, wherein the effectiveness of the current drug delivery system is assessed by comparing the one or more medical images and determining a degree to which a tumor or lesion has regressed.

12. The method of claim 10, wherein the reconfiguring the drug administration includes systematically adjusting one or more of a drug amount, a drug concentration, a drug administration location, a drug administration frequency, a route of drug administration, an administration time, a type of therapy, or a combination thereof, in order to increase the effectiveness of the current drug delivery system.

13. A system for estimating drug delivery at a target tissue, the system comprising:
at least one data storage device storing instructions for estimating drug delivery at a target tissue; and
at least one processor configured to execute the instructions to perform a method including:
receiving a patient-specific anatomical model of at least one vessel of the patient and a target tissue where a drug is to be supplied;
receiving patient-specific information defining administration of a drug to the patient;
identifying one or more locations in the target tissue where drug delivery data will be computed;

deriving patient-specific data from the patient-specific anatomical model and/or the patient, the patient-specific data including one or more physiological conditions;

determining, by measuring or calculating, one or more personalized blood flow characteristics in a vascular network leading to the one or more locations in the target tissue where drug delivery data will be computed, using the patient-specific anatomical model, patient-specific information defining the administration of the drug and the patient-specific data including the one or more physiological conditions;

simulating drug delivery by virtually modeling the administration of drug particles into the vascular network of the patient-specific anatomical model upstream from the one or more locations in the target tissue;

calculating a transportation, spatial, and/or temporal distribution of the drug particles in one or more locations of the vascular network using size and amount of the drug particles, one or more equations describing drug transport, the patient-specific information defining the administration of the drug including size and amount of the drug particles, and calculated one or more personalized blood flow characteristics, wherein the amount of the drug particles are calculated based on a prescribed dosage of the drug;

determining a ratio of the drug particles reaching the target tissue to the drug particles administered in total based on the calculating the distribution of the drug particles to the one or more locations of the vascular network and the calculated one or more personalized blood flow characteristics;

computing personalized drug delivery data at the one or more locations in the target tissue of the patient-specific anatomical model using the patient-specific data derived from the patient-specific anatomical model and the transportation, spatial, and/or temporal distribution of the drug particles, the personalized drug delivery data including a circulatory destination probability of the drug particles administered into the vascular network leading to the target tissue based on the ratio of the drug particles reaching the target tissue to the drug particles administered in total;

outputting the personalized drug delivery data in three-dimensional display overlaid on the patient-specific anatomical model to an electronic storage medium and/or display medium; and modifying drug administration to cause the computed personalized drug delivery data including the ratio of the drug particles reaching the target tissue to the drug particles administered in total in the target tissue to be within a range of desired drug delivery data in the target tissue.

14. The system of claim 13, wherein the personalized blood flow characteristics include, one or more of,
a velocity field of blood flow in the patient's vasculature,
an estimated blood supply in the patient's vasculature, or
any patient-specific hemodynamic characteristic that affects the distribution of drug particles along the vascular network.

15. The system of claim 13, wherein the processor is further configured for:
receiving the desired drug delivery data in the target tissue; and
assessing effectiveness of a current drug delivery system by comparing the computed personalized drug delivery data including the ratio of the drug particles reaching the target tissue to the drug particles administered in total in the target tissue with the desired drug delivery data in the target tissue.

16. The system of claim 13, further including:
receiving, at different time points, one or more medical images of patients;
extracting patient-specific data from the one or more medical images;
assessing an effectiveness of the current drug delivery system by comparing the patient-specific data extracted from the one or more medical images; and
reconfiguring the drug administration in order to increase effectiveness of a current drug delivery system.

17. A non-transitory computer-readable medium for use on a computer system containing computer-executable programming instructions executing a method for estimating drug delivery at a target tissue where a drug is to be supplied, comprising:
receiving a patient-specific anatomical model of at least one vessel of the patient and a target tissue;
receiving patient-specific information defining administration of a drug to the patient;
identifying one or more locations in the target tissue where drug delivery data will be computed;
deriving patient-specific data from the patient-specific anatomical model and/or the patient, the patient-specific data including one or more physiological conditions;
determining, by measuring or calculating, one or more personalized blood flow characteristics in a vascular network leading to the one or more locations in the target tissue where drug delivery data will be computed, using the patient-specific anatomical model, patient-specific information defining the administration of the drug and the patient-specific data including the one or more physiological conditions;
simulating drug delivery by virtually modeling the administration of drug particles into the vascular network of the patient-specific anatomical model upstream from the one or more locations in the target tissue;
calculating a transportation, spatial, and/or temporal distribution of the drug particles in one or more locations of the vascular network using size and amount of the drug particles, one or more equations describing drug transport, the patient-specific information defining the administration of the drug including size and amount of the drug particles, and calculated one or more personalized blood flow characteristics, wherein the amount of the drug particles are calculated based on a prescribed dosage of the drug;
determining a ratio of the drug particles reaching the target tissue to the drug particles administered in total based on the calculating the distribution of the drug particles to the one or more locations of the vascular network and the calculated one or more personalized blood flow characteristics;
computing personalized drug delivery data at the one or more locations in the target tissue of the patient-specific anatomical model using the patient-specific data derived from the patient-specific anatomical model and the transportation, spatial, and/or temporal distribution of the drug particles, the personalized drug delivery data including a circulatory destination probability of the drug particles administered into the vascular network leading to the target tissue based on the ratio of the drug particles reaching the target tissue to the drug particles administered in total;

outputting the personalized drug delivery data in three-dimensional display overlaid on the patient-specific anatomical model to an electronic storage medium and/or display medium; and modifying drug administration to cause the computed personalized drug delivery data including the ratio of the drug particles reaching the target tissue to the drug particles administered in total in the target tissue to be within a range of desired drug delivery data in the target tissue.

18. The non-transitory computer-readable medium of claim 17, wherein the blood flow characteristics include, one or more of, a velocity field of blood flow in the patient's vasculature, an estimated blood supply in the patient's vasculature, or any patient-specific hemodynamic characteristic that affects the distribution of drug particles along the vascular network.

19. The non-transitory computer-readable medium of claim 17, further including:

receiving the desired drug delivery data in the target tissue; and assessing effectiveness of a current drug delivery system by comparing the computed personalized drug delivery data including the ratio of the drug particles reaching the target tissue to the drug particles administered in total in the target tissue with the desired drug delivery data in the target tissue.

20. The non-transitory computer-readable medium of claim 17, further including:

receiving, at different time points, one or more medical images of patients;

extracting patient-specific data from the one or more medical images;

assessing an effectiveness of the current drug delivery system by comparing the patient-specific data extracted from the one or more medical images; and reconfiguring the drug administration in order to increase effectiveness of a current drug delivery system.

* * * * *